(12) United States Patent
Desai et al.

(10) Patent No.: US 8,475,489 B2
(45) Date of Patent: *Jul. 2, 2013

(54) APPARATUS FOR OCCLUDING BODY LUMENS

(75) Inventors: Rupesh Desai, San Jose, CA (US); Alexander L. Huang, Menlo Park, CA (US); Steven Yee, Sunnyvale, CA (US); Jennifer Hodor, Sunnyvale, CA (US)

(73) Assignee: Percutaneous Systems, Inc., Palo Alto, CA (US)

( * ) Notice: Subject to any disclaimer, the term of this patent is extended or adjusted under 35 U.S.C. 154(b) by 1227 days.

This patent is subject to a terminal disclaimer.

(21) Appl. No.: 12/041,241

(22) Filed: Mar. 3, 2008

(65) Prior Publication Data

US 2009/0018569 A1 Jan. 15, 2009

Related U.S. Application Data

(63) Continuation-in-part of application No. 11/777,522, filed on Jul. 13, 2007, now Pat. No. 7,879,066.

(51) Int. Cl.
*A61M 29/00* (2006.01)
(52) U.S. Cl.
USPC .......................................... 606/200; 606/127
(58) Field of Classification Search
USPC .................. 606/127, 191, 200; 128/830, 831, 128/842, 843
See application file for complete search history.

(56) References Cited

U.S. PATENT DOCUMENTS

| | | | |
|---|---|---|---|
| 2,756,752 A * | 7/1956 | Scherlis | 606/127 |
| 4,046,149 A | 9/1977 | Komiya | |
| 4,262,677 A | 4/1981 | Bader | |
| 4,295,464 A | 10/1981 | Shihata | |
| 4,706,671 A | 11/1987 | Weinrib | |
| 4,807,626 A * | 2/1989 | McGirr | 606/127 |
| 5,108,420 A * | 4/1992 | Marks | 606/213 |
| 5,135,534 A | 8/1992 | Tulip | |
| 5,192,286 A | 3/1993 | Phan et al. | |
| 5,303,714 A * | 4/1994 | Abele et al. | 600/585 |

(Continued)

FOREIGN PATENT DOCUMENTS

| | | |
|---|---|---|
| DE | 10031661 A1 | 1/2002 |
| EP | 0 605 427 B1 | 12/1992 |

OTHER PUBLICATIONS

Bard Urological Division Catalog 1990, PA24, "Woven Blasucci Ureteral Catheters", 3 pages.

(Continued)

*Primary Examiner* — Gary Jackson
*Assistant Examiner* — Jonathan Hollm
(74) *Attorney, Agent, or Firm* — Wilson, Sonsini, Goodrich & Rosati (57) ABSTRACT

A luminal occlusion device comprises a tension member, an elongate shaft, and a flat film having an axial receptacle which is received over a distal portion of the tension member. The flat film has proximal and distal ends which are attached to the distal ends of the tension member and the elongate shaft, respectively. Thus, distal advancement of the tension member relative to the shaft will cause the flat film to assume a low profile configuration, while proximal retraction of the tension member relative to the elongate shaft will cause the flat film to assume a foreshortened, compacted configuration. The film usually includes one or more radioopaque markers which help shape the compacted film.

35 Claims, 9 Drawing Sheets

U.S. PATENT DOCUMENTS

| | | | |
|---|---|---|---|
| 5,431,676 A | 7/1995 | Dubrul et al. | |
| 5,454,790 A | 10/1995 | Dubrul | |
| 5,531,717 A | 7/1996 | Roberto et al. | |
| 5,676,688 A | 10/1997 | Jaker et al. | |
| 5,711,841 A | 1/1998 | Jaker | |
| 5,814,058 A | 9/1998 | Carlson et al. | |
| 5,827,201 A * | 10/1998 | Samson et al. | 600/585 |
| 5,836,913 A | 11/1998 | Orth et al. | |
| 5,897,535 A | 4/1999 | Feliziani et al. | |
| 5,989,264 A | 11/1999 | Wright | |
| 6,007,488 A | 12/1999 | Jaker et al. | |
| 6,056,769 A | 5/2000 | Epstein et al. | |
| 6,066,149 A * | 5/2000 | Samson et al. | 606/159 |
| 6,080,174 A | 6/2000 | Dubrul et al. | |
| 6,171,329 B1 * | 1/2001 | Shaw et al. | 606/213 |
| 6,214,037 B1 | 4/2001 | Mitchell et al. | |
| 6,240,968 B1 | 6/2001 | Bigonzi-Jaker et al. | |
| 6,325,812 B1 | 12/2001 | Dubrul et al. | |
| 6,494,893 B2 | 12/2002 | Dubrul et al. | |
| 6,500,182 B2 | 12/2002 | Foster | |
| 6,520,983 B1 | 2/2003 | Colgan et al. | |
| 6,656,146 B1 | 12/2003 | Clayman et al. | |
| 6,780,197 B2 | 8/2004 | Roe et al. | |
| 6,800,080 B1 * | 10/2004 | Bates | 606/127 |
| 6,929,664 B2 | 8/2005 | Kolb | |
| 6,945,950 B2 | 9/2005 | Clayman et al. | |
| 7,044,134 B2 | 5/2006 | Khairkhahan et al. | |
| 7,052,507 B2 | 5/2006 | Wakuda et al. | |
| 7,214,229 B2 | 5/2007 | Mitchell et al. | |
| 7,217,250 B2 | 5/2007 | Kolb | |
| 7,229,461 B2 | 6/2007 | Chin et al. | |
| 7,879,066 B2 | 2/2011 | Desai et al. | |
| 2001/0044595 A1 | 11/2001 | Reydel et al. | |
| 2002/0183853 A1 | 12/2002 | Mitchell et al. | |
| 2003/0120281 A1 | 6/2003 | Bates et al. | |
| 2004/0215230 A1 | 10/2004 | Frazier et al. | |
| 2004/0236368 A1 * | 11/2004 | McGuckin et al. | 606/200 |
| 2005/0197627 A1 | 9/2005 | Huang et al. | |
| 2005/0228417 A1 * | 10/2005 | Teitelbaum et al. | 606/159 |
| 2005/0228481 A1 | 10/2005 | Manasas et al. | |
| 2005/0277980 A1 | 12/2005 | Yassinzadeh | |
| 2006/0009784 A1 * | 1/2006 | Behl et al. | 606/113 |
| 2006/0200047 A1 * | 9/2006 | Galdonik et al. | 600/585 |
| 2007/0016244 A1 | 1/2007 | Behl et al. | |
| 2007/0106233 A1 | 5/2007 | Huang et al. | |
| 2007/0173882 A1 | 7/2007 | Spurchise | |
| 2007/0191768 A1 | 8/2007 | Kolb | |

OTHER PUBLICATIONS

Garrido et al., "Utilización del catéter "stone sweeper" en la patologia litiásica del tracto urinario superior," [The use of Stone Sweeper catheter for stone disease of the upper urinary tract], Arch Esp Urol. Nov. 2006; 56(9):889-892. [English Abstract Only].

L'Esperance et al., "Ureteral Expanding Stent: A New Device for Urolithiasis," J Endourol. May 1, 2007; 21(5): 533-537.

Woitzik et al., "Polyethylene sheath device to reduce tumor cell seeding along the needle tract in percutaneous biopsy," (2003) Surg. Endosc. 17:311-314.

International Search Report and Written Opinion of PCT Application No. PCT/US2008/069482, dated Sep. 8, 2008, 9 pages total.

\* cited by examiner

APPARATUS FOR OCCLUDING BODY LUMENS

CROSS-REFERENCES TO RELATED APPLICATIONS

The present application is a continuation-in-part of application Ser. No. 11/777,522, filed on Jul. 13, 2007, the full disclosure of which is incorporated herein by reference. The present application is also related to but does not claim the benefit of copending application Ser. No. 10/886,886,filed on Jul. 7, 2004 and Ser. No. 11/777,515, filed on Jul. 13, 2007, the full disclosures of which are incorporated herein by reference.

BACKGROUND OF THE INVENTION

1. Field of the Invention

The present invention relates generally to medical apparatus. More particularly, the present invention relates to apparatus for treating ureters and other body lumens.

It is common for kidney stones to pass from the kidney through the ureter to the urinary bladder. While muscular peristalsis of the ureter will often pass the stones into the bladder without complication, in some instances large and/or irregularly shaped stones may become lodged within the ureter causing discomfort and potential damage to the ureter and upper collective system.

A number of ways have been proposed for dislodging such kidney stones. For example, extracorporeal shock wave lithotripsy (ESWL) can be used to break up the kidney stones but is often ineffective when the stones are present in the ureter. Moreover, ESWL can produce irregularly-shaped fragments which, while smaller than the original stone, may have sharp edges that will prevent spontaneous passage of the particles through the ureter. In the case of a stone or fragment impacted in the ureter, it is common practice to attempt capture, using a wire stone basket. The basket is introduced through a ureteroscope which itself is typically introduced retrograde through the urinary tract.

In many cases, further lithotripsy through the scope is performed (ISWL). It is often difficult to advance such stone baskets past the obstructing material. Attempts to pass wire baskets or other grasping apparatus past a stone lodged in the ureter also presents risk of damage to the ureter. Abrasion, stretching, or perforation of the ureter at the impaction site can cause local urine leakage or edema even if the stone or resulting debris is successfully captured; and removal of the basket with the stone may be quite difficult. In some instances, baskets containing captured stones or fragments cannot themselves be removed, and it is difficult if not impossible to release the captured stone material back into the lumen of the ureter. In those cases, the basket must often be retrieved surgically. Finally, if and/or when ISWL is performed, it would be useful to have some means of stabilizing stone fragments at the treatment site, rather than letting them escape up the ureter in a retrograde direction.

As an improvement over lithotripsy and the use of baskets for collecting kidney stones and debris, it has recently been proposed to use a compacted length of material to form an occluding structure within a ureter. The compacted length of material can be used to either directly draw and remove the kidney stone from the ureter into the bladder. Alternatively, the compacted length of material can be used to contain fragments which are produced in an energy-based lithotripsy procedure. As described in prior copending application Ser. No. 10/866,866, the length of material can be an everting tubular member, a flat membrane which folds as an accordion structure, can or take a variety of other configurations. None of the prior described occlusion structures, however, has been optimum in all respects.

For these reasons it would be desirable to provide improved apparatus for deploying and compacting a length of material in order to occlude a body lumen, such as a ureter, when performing procedures for the removal and/or lithotripsy of kidney stones. In particular, it would be desirable to provide apparatus having material lengths which may be delivered in a very low profile configuration while permitting deployment into a relatively high volume configuration having a substantial density and ability to conform to symmetric and non-symmetric body lumens to help assure effective occlusion of the body lumen, particularly occlusion of ureters to prevent the passage of kidney stones and kidney stone fragments. The apparatus should also be atraumatic in use, require significantly less skill than basket manipulation, optionally allow the release of captured material, should be simple and economical in construction and use, and should provide minimum risk and trauma to the patient. At least some of these objectives will be met by the inventions described hereinbelow.

2. Description of the Background Art

The use of an everting sleeve composed of thin, tensilized polytetrafluoroethylene for introducing catheters to body lumens is described in U.S. Pat. Nos. 5,531,717; 5,676,688; 5,711,841; 5,897,535; 6,007,488; 6,240,968; and EP605427B1. A wire basket for preventing stone fragment movement through a body lumen during lithotripsy procedure is available under the Stone Cone tradename from Boston Scientific Corporation. See Published U.S. Application No. 2003/0120281. Copending application Ser. No. 10/794, 337, filed on Mar. 5, 2004, the full disclosure of which is incorporated herein by reference, describes a sheet delivery system that could be used in performing some of the methods described herein.

BRIEF SUMMARY OF THE INVENTION

The present apparatus provides an improved luminal occlusion device, comprising a tension member, an elongate shaft, and a flat film having an axial receptacle for receiving a distal portion of the tension member. The tension member has a proximal end and a distal end, and is typically formed as a solid core wire having the dimensions and properties generally associated with smaller guidewires, such as uretal guidewires. The elongate shaft serves as a guide structure for the tension member and will usually comprise a hollow tube, such as a hollow polymeric tubular body, having a distal end and a proximal end. The tension member is slidably received within a lumen of the elongate shaft, and the distal end of the tension member is able to extend distally from the distal end of the shaft and axially translate relative to the elongate shaft. The axial receptacle of the flat film will then be disposed over the tension member and will typically have a proximal end fixed or otherwise coupled to a distal end of the elongate shaft and a distal end fixed or otherwise coupled to a distal location on the tension member. Thus, the flat film can be axially elongated and placed in a low profile configuration by advancing the tension member distally relative to the elongate shaft. Conversely, the flat film can be compacted into a high volume configuration by proximally drawing the tension member relative to the elongate shaft. By having the axial receptacle of the film positioned over or otherwise anchored along the tension member, the stability of the deployment is improved.

In particular embodiments of the present invention, the flat film has characteristics which are further selected to improve the effectiveness of the deployment. The film will preferably be elastic so that it may elongate and "neckdown" as it is stretched by distal advancement of the tension member. The film may consist of a single layer or flat sheet, but will more usually comprise two or more layers which have been laminated to form the film with an axial sleeve or other receptacle defining an axis thereof. The film will usually be symmetric, extending from the axial receptacle in a pair of "wing" structures, where the wing structures may have a variety of specific configurations as illustrated in detail hereinbelow. In other instances, however, the film may be asymmetric relative to the axial receptacle, in some cases consisting only of a single wing or structure extending from one side of the axial receptacle. The film may be formed from a variety of materials, typically being a polymer, such as a polyethylene, nylon, silicone, spun olefin, but preferably being a polyurethane film that is resilient, elastic, and which has a "low notch sensitivity" which allows it to withstand laser impingement without significant degradation during lithotripsy protocols. Optionally, the film may be formed from layers of different materials, may include reinforcement filaments, braids, webs, or the like.

In an illustrated embodiment, the flat film will typically have parallel edges which are spaced apart by a distance in the range from 2 mm to 15 mm and will have a length in the axial direction in the range from 10 mm to 100 mm. Preferred flat films will comprise one or more polymeric sheet(s) having a total thickness in the range from 0.1 mm to 0.5 mm. It has been found that sheets with these characteristics will have a very low profile elongated configuration to facilitate introduction into the body lumen, particularly into ureters and past kidney stones, as well as having a deployed, high-volume configuration which is symmetric and particularly suitable for deployment and occlusion within a ureter.

In another particular aspect of the present invention, the flat film will comprise at least one elongate element formed therein or on a surface thereof. Typically, the elongate element will be located along at least one of the axial edges (e.g., parallel to and spaced inwardly from the edge), and more typically, one elongate element will be provided along each of the two edges of the flat film. In most preferred embodiments, flat film includes a first wing portion formed on one side of the axial receptacle and a second wing portion formed on the other side of the axial receptacle. A first elongate element is disposed along an outer edge of the first wing and a second elongate element is disposed along an outer edge of the second wing. In some embodiments, two or more elongate elements may be placed in parallel and/or in series along the edge(s).

The elongate elements may serve various purposes. In certain embodiments, the elongate elements will comprise radioopaque markers. In other embodiments, the elongate elements may comprise primarily structural elements, such as nitinol or other elastic wires which are arranged to deform or stretch the film radially outwardly with respect to the axial receptacle. In other instances, the elongate elements may serve both purposes and/or individual elements serving each purpose may be present on the film. In one specific embodiment, first and second wires are attached to the outer edge of each wing of the flat film, where the wires preferentially collapse into helical structures as the film is foreshortened by proximal retraction of the tension member. Such structures provide a very large and generally circular occlusion component within the body lumen after deployment.

In a specific embodiments, the radioopaque markers may have different mechanical properties than those of the film. In particular, the markers may be more rigid or stiff than the film, causing the film to collapse or fold in a manner different from what would occur without the marker. For example, the metal foil markers disposed along opposite edges of the film will cause the film to rotate as it collapses, thus forming a higher volume and less collapsible occlusion than would be formed with a simple accordion-type fold. Gold foil is an ideal material for this application as it is dense and highly radioopaque, can be utilized as a very thin foil, and while being stiffer than the thin film, is still quite flexible. However, other materials in strips, films, foil, or wires could also be utilized, with or without requiring high radioopacity. For example, thin shape memory wires, such as nickel titanium wires, could be pre-shaped or "programmed" to take a particular shape or to fold in a particular sequence/shape when released from tension, and put under compression. Shaping of the compacted film could also be accomplished by screening a relatively thick layer of ink on the film in strips or in a geometric pattern.

In certain embodiments of the present invention, the luminal occlusion device will further comprise a distal tip extending distally from the distal end of the tension member. The distal tip will be relatively soft and facilitate atraumatic introduction on the occlusion device through a body lumen, particularly through a ureter past a kidney stone. Usually, the distal tip will comprise a polymeric tube which tapers down in the distal direction, and the polymeric tube will comprise a polymer, such as polyurethane, having a durometer in the range from 25 D to 55 D.

The tension member will typically comprise a solid core wire, usually having a width in the range from about 0.2 to about 0.6 mm. In other cases, however, the tension member could comprise a hollow core wire, could have dimensions which are larger or smaller than those cited above.

In preferred aspects of the present invention, the elongate shaft will comprise a polymeric tube having an outside width in the range from 0.5 mm to 1.5 mm and a length in the range from 50 cm to 250 cm. The polymeric tube may comprise any of a variety of polymers, typically being a polyether block amide having a durometer in the range from 50 D to 80 D. In many cases, at least a portion of the polymer tube will be reinforced, and in particular embodiments the entire polymeric tube is reinforced with a steel braid.

The occlusion device will typically have a handle at or near its proximal end. In preferred embodiments, the handle is removably attachable to the proximal end of the elongate shaft and is positioned over a proximal end of the tension member. In such cases, the handle allows manipulation of the occlusion device while it is being introduced into the ureter or other body lumen. The handle also prevents accidental deployment of the tension member since it covers and protects the distal end. Thus, in use, the handle will be moved after the occlusion device has been positioned within the body lumen at its target location. After the handle is removed, the proximal end of the tension member is exposed so that the user may manually grasp the proximal end, and pull on it in a proximal direction in order to deploy the flat film. Usually, the proximal end of the tension member will be modified to provide a gripping surface to facilitate manual deployment.

In still further aspects of the present invention, the tension member may be modified or additional components provided in order to lock or hold the flat film in its deployed configuration after the tension member has been pulled proximally. For example, a detent structure may be formed at or near the proximal end of the tension member, where the detent expands when the tension member is proximally retracted to deploy the film. The expanded detent thus blocks or inhibits inadvertent distal movement of the tension member which would unintentionally return the flat film to its low profile configuration. The detent may comprise, for example, a bend in the tension member, such as a short serpentine section.

The flat films may have a variety of specific geometries. As discussed above, often the flat film will include first and second wings, where the wings are generally rectangular or trapezoidal and symmetrically disposed about the axial receptacle. The wings, however, need not be symmetric and need not have straight or flat edges. Moreover, the films may be modified to affect the geometry or shape of the film as it is compacted. For example, the film may include one or more slits. When the slits are oriented wholly or partially axially, they facilitate radial expansion of the film, allowing the film to assume a greater effective radius than might have been possible without the slits. When the slits are oriented wholly or partially laterally, in contrast, they will facilitate axial stretching of the film as the tension member is distally translated, allowing the film to assume an even narrower profile for advancement through the ureter or other body lumen.

In a particular embodiment, the flat film comprises a first winged region and a second winged region, where the winged regions are axially separated by a narrowed or waist region. Nitinol or other highly elastic wires are embedded into the radially outward edges of the winged regions as well as the narrowed or waist region therebetween. The elastic wires maintain the winged regions in a flat or outwardly deployed configuration when the flat film is in its elongated position. It will be appreciated that the winged regions will easily collapse against the elongate shaft which carries them as it is being introduced through the ureter, other body lumen, or delivery sheath or cannula. Once at a target location within the urethra or other body lumen, the flat film may be axially collapsed so that the winged regions are compacted into two axially spaced-apart structures, typically having the elastic wires form into two, separate helical windings. The waist portion of the flat film, however, will typically be reinforced or otherwise prevented from axially collapsing so that there is a space between the two compacted regions. Such axially spaced-apart compacted structures provide for "dual" sweeping where any stone fragments which bypass the leading compacted structure can be caught by the trailing structure.

DETAILED DESCRIPTION OF THE INVENTION

Figure 1:
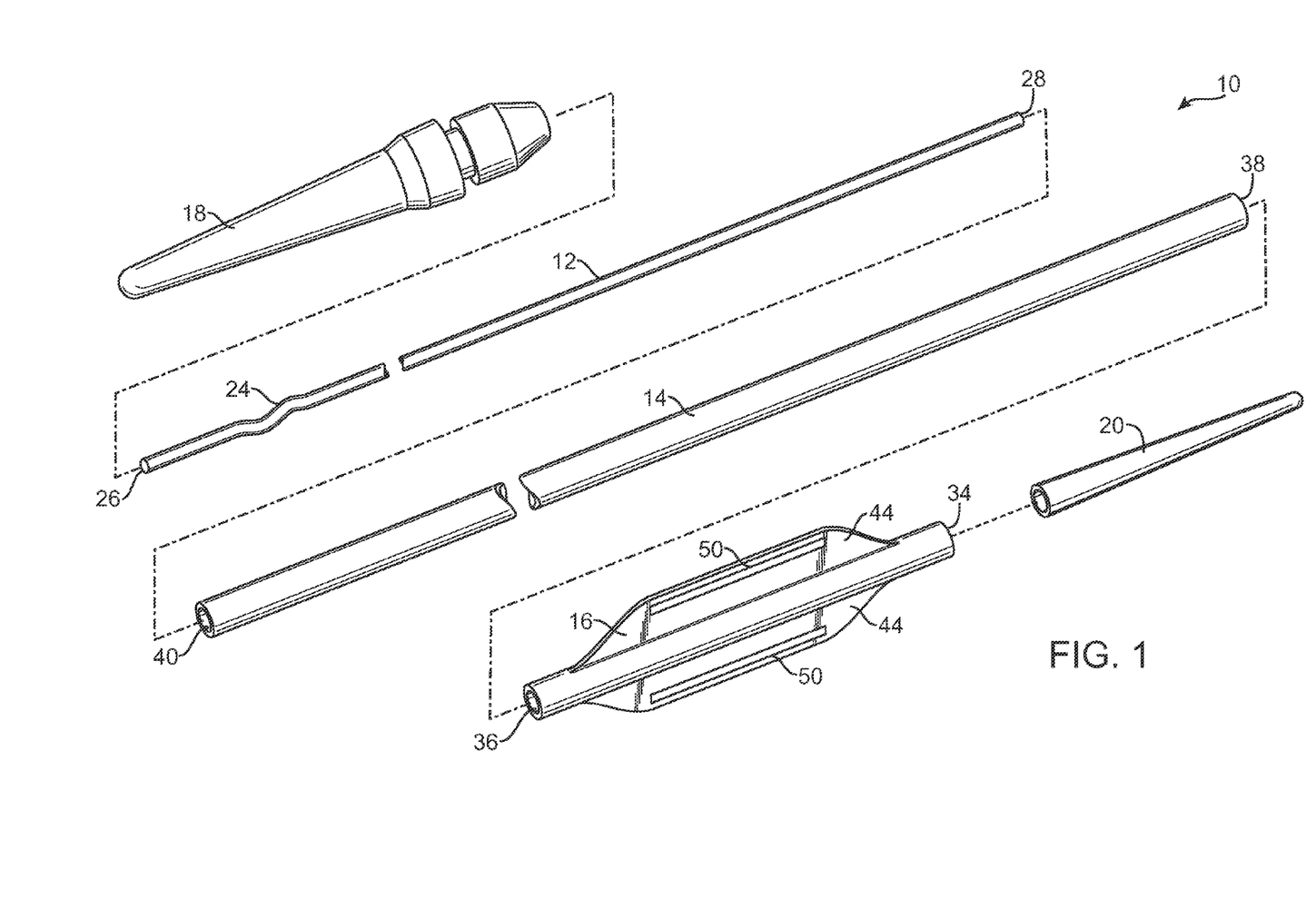
FIG. 1 is an exploded view of a luminal occlusion device constructed in accordance with the principles of the present invention.
Figure 2:
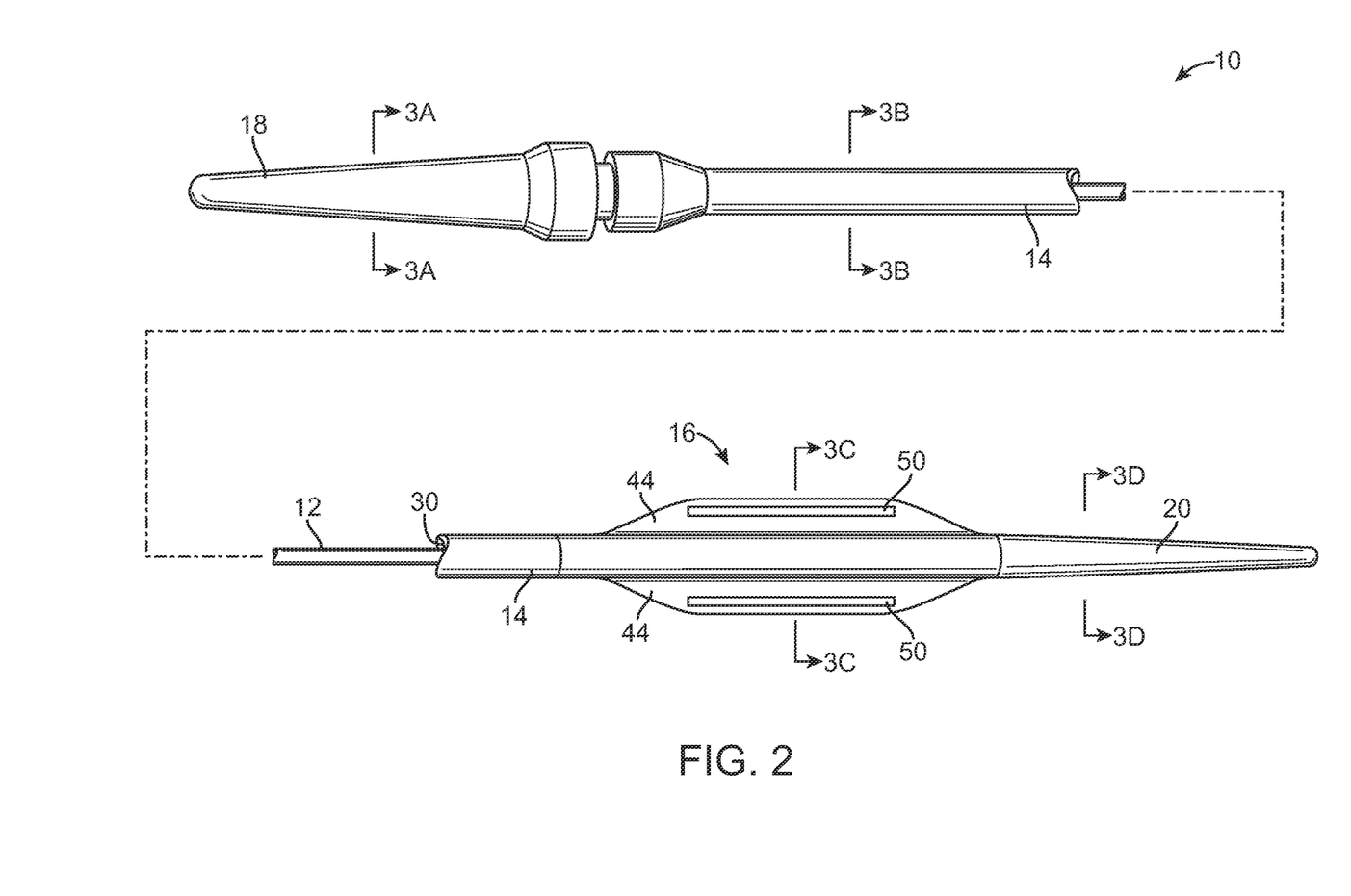
FIG. 2 illustrates the luminal occlusion device of FIG. 1 in its assembled configuration with portions broken away.
Figure 3A:
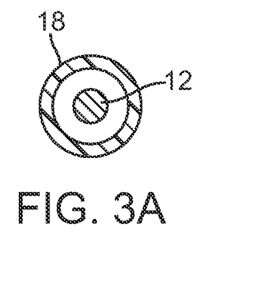
FIGS. 3A-3D are cross-sectional drawings taken along lines 3A to 3D in FIG. 2.
Figure 3B:
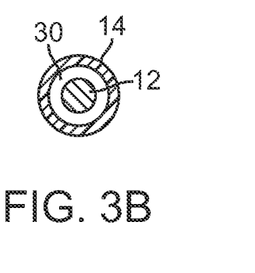
Figure 3C:
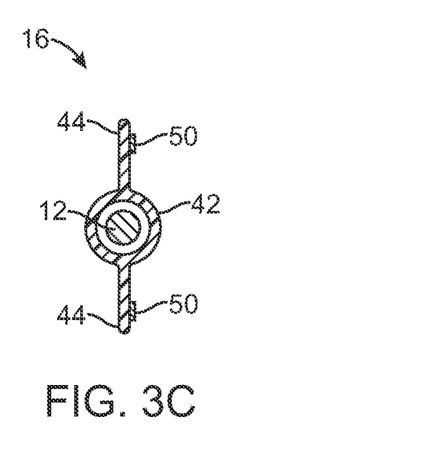
Figure 3D:
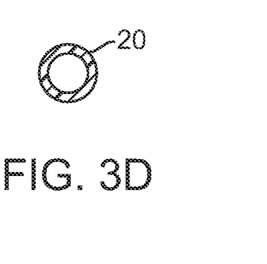
Figure 5:
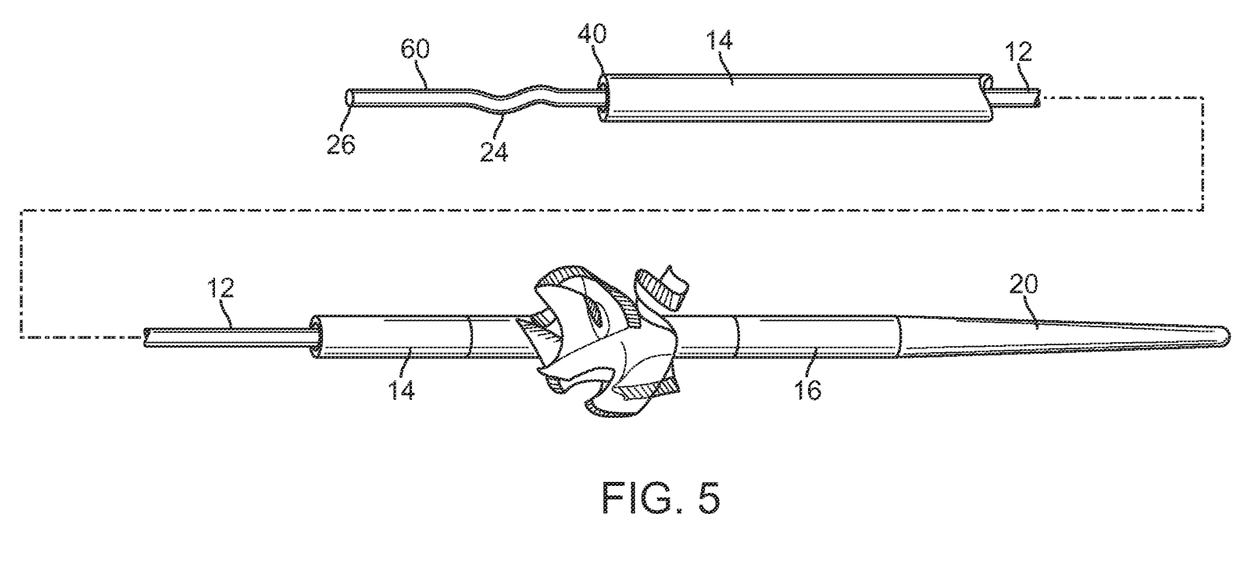

As illustrated in FIGS. 1, 2, and 3A-3D, an exemplary luminal occlusion device 10 constructed in accordance with the principles of the present invention, comprises a tension member 12, an elongate shaft 14, a flat film 16, a handle 18, and a distal tip 20. The tension member 12 comprises a solid core wire, typically composed of stainless steel or nickel-titanium alloy, having a length in the range set forth above. A serpentine detent 24 is formed near a proximal end 26 thereof. The distal end 28 of the tension member will pass through a lumen 30 of the elongate shaft 14, as best seen in FIGS. 2 and 3B. The distal end 28 is connected to a distal end 34 of the flat film 16, while a distal end 38 of the elongate shaft 14 is connected to a proximal end 36 of the flat film. The distal portion of the tension member 12 passes through an axial receptacle 42 of the flat film 16, as best seen in FIG. 3C, and proximal retraction of the tension member 12 relative to elongate shaft 14 will thus cause the axial receptacle 42 to bunch up on the tension member, thus compacting the opposed wings 44, causing them to deploy, as best illustrated in FIG. 5 discussed below. A pair of radioopaque markers 50 are formed on the flat film 16, typically being gold foil strips which are glued, bonded, or otherwise attached to the wings 44. Additional radioopaque markers 52 and 54 are formed on the distal ends of the tension member 12 and elongate shaft 14, respectively. The distal tip 20 is also attached to the distal end 28 of the tension member 12, although the tip will usually have a hollow lumen, as best seen in FIG. 3D.

Figure 4:
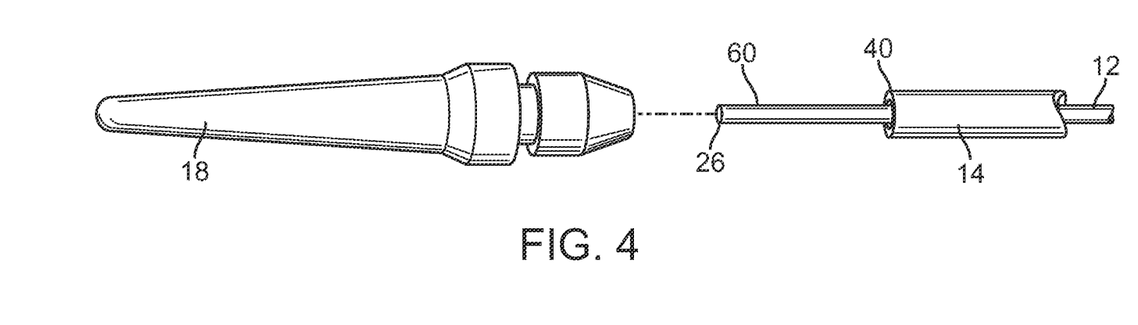
FIGS. 4 and 5 illustrate the steps which are taken to deploy a flat film on the luminal occlusion device of FIGS. 1 and 2.

The flat film 16 on the luminal occlusion device 10 may be deployed in a simple, two-step procedure. As illustrated in FIG. 4, the handle 18 is first removed from the proximal end 40 of the elongate shaft 14, exposing a gripping surface 60 at the proximal end 26 of the tension member 12. The user may then deploy the film 16 by grasping the elongate shaft 14 near the proximal end 40 with one hand and grasping the gripping surface 60 on the tension member 12 with the other hand. The gripping surface 60 is then proximally withdrawn relative to the elongate shaft 14 which causes the distal end 28 of the tension member to move toward the distal end 38 of the elongate shaft. This foreshortening causes the film 16, which is captured between these two ends, to axially shorten and compact, as shown in FIG. 5. As the distal end 28 of the tension member 12 is drawn proximally relative to the elongate shaft 14, the radioopaque markers 52 and 54 can be observed to move toward each other and will define the leading and trailing ends of the film 16 after it is compacted. The combination of the flat film and the axial markers, preferably having a stiffness greater than that of the film, causes a high volume and resilient structure which is capable of conforming to and effectively occluding the body lumen deployment, as illustrated.

Figure 6:
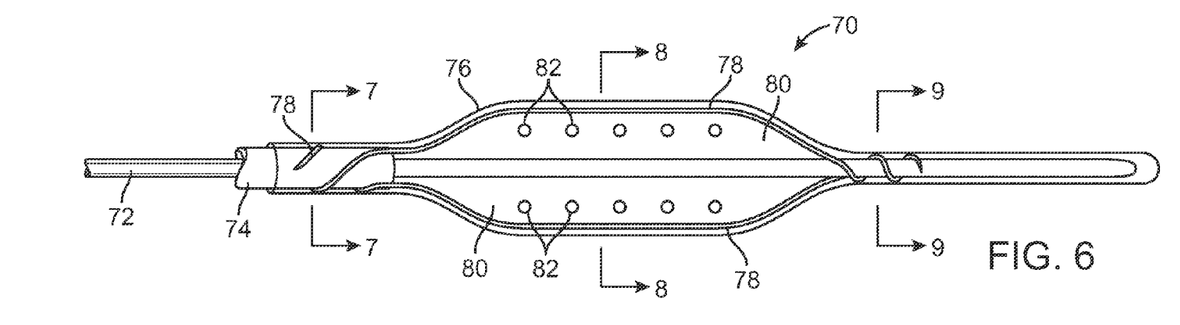
FIG. 6 illustrates an additional embodiment of a luminal occlusion device constructed in accordance with the principles of the present invention.
Figure 7:
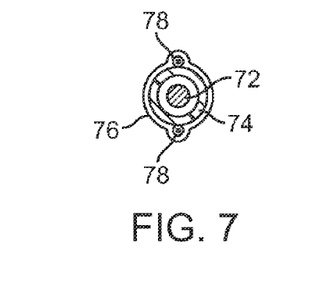
FIGS. 7, 8, and 9 are cross-sectional views taken along lines 7-7, 8-8, and 9-9 of FIG. 6, respectively.
Figure 8:
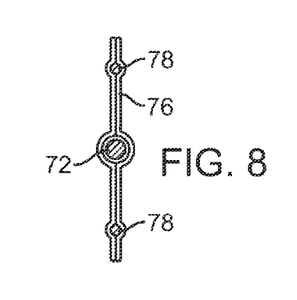
Figure 9:
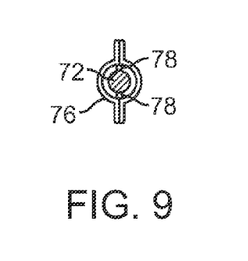
Figure 10:
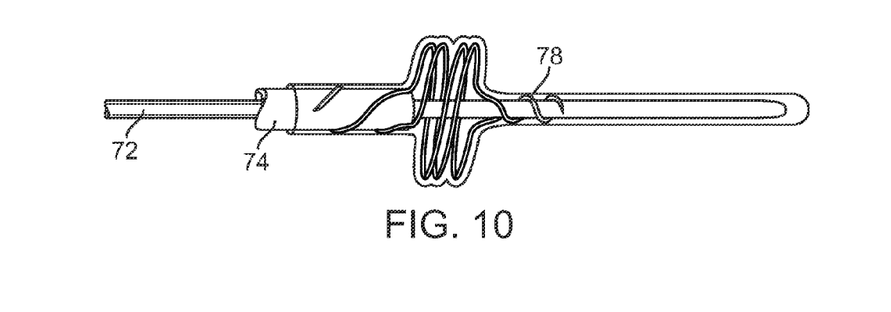
FIG. 10 illustrates the luminal occlusion device of FIG. 6, shown with a flat film in its compacted configuration.

An alternative luminal occlusion device 70 includes a tension member 72 and an elongate shaft 74 constructed generally as described above with respect to the embodiment of FIG. 1. Note that the proximal portion of the device is not shown as it will be identical to that shown in FIG. 1. A flat film 76 is also similar to film 16 shown in FIG. 1, except that it includes at least one peripheral wire 78 along the outer edge of each of two wings 80. The wires 78 extend over and are attached to the distal end of the elongate shaft 14, typically being helically wound over the outer surface of the distal end of said shaft. Similarly, the wires 78 are wrapped around the tension member 72 near the distal end thereof, again being helically wound to facilitate attachment. The wires 78 will be highly elastic, typically being composed of nickel titanium alloy (nitinol) or other highly elastic alloy. When the tension member 72 is distally advanced relative to the shaft 74, the wires will collapse inwardly, helping reduce the profile of the film 76 as it is being introduced. Conversely, when the tension member 72 is proximally retracted relative to the elongate shaft 14, as shown in FIG. 10, the peripheral wires 78 will axially collapse or foreshorten into a generally helical configuration, providing a compacted structure having a generally circular outer periphery with excellent occlusion characteristics. That is, the helical shape of the wire 78 will uniformly wrap the film 76 over the tension member 72 leaving few gaps or openings to compromise the occlusion. Film 76 has a plurality of individual radioopaque markers 82 formed along each edge adjacent the wires 78. It would also be possible, of course, to employ strip radioopaque markers as shown in previous embodiments.

Figure 11A:
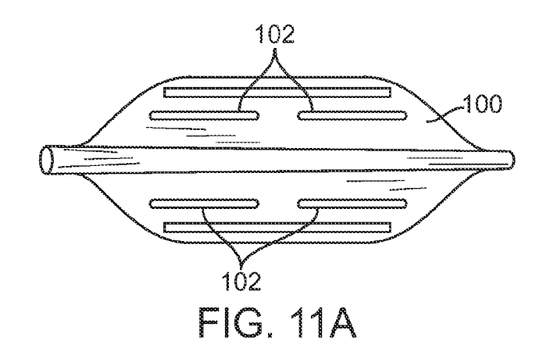
FIGS. 11A and 11B illustrate a flat film useful in the luminal occlusion devices of the present invention, where the film includes axial slits, with the film shown in its relaxed configuration in FIG. 11A and in its partially foreshortened configuration in FIG. 11B.
Figure 11B:
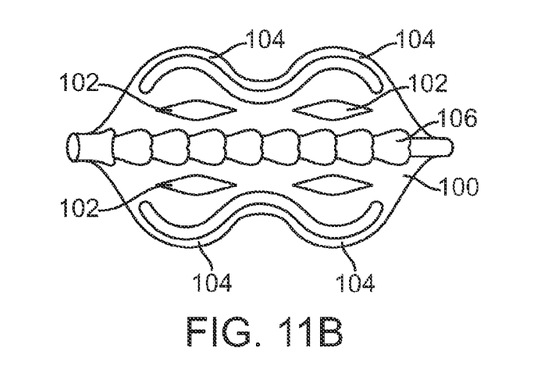

As illustrated thus far, the flat films have generally had symmetric, regular geometries. The films have also been continuous without gaps or other disruptions. In other embodiments, the films may be asymmetric, and/or may have slits or other discontinuities formed in their surfaces. For example, as shown in FIGS. 11A and 11B, a flat film 100 which is formed similarly to film 16 in FIG. 1, may include a plurality of axial slits 102. As the film is axially foreshortened, as illustrated in FIG. 11B, the slits 102 will open allowing portions 104 on the film to extend radially further away from the axial receptacle 106 than would have been possible in the absence of the slits. In this way, the film 100 may assume a larger compacted diameter than would have been possible without the slits.

Figure 12A:
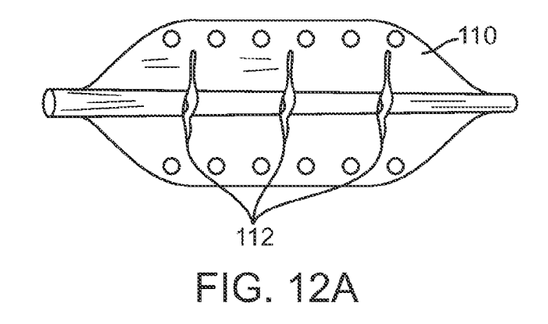
FIGS. 12A and 12B illustrate a further example of a flat film useful in the luminal occlusion devices of the present invention, where the flat film includes lateral slits. The film is shown in its relaxed configuration in FIG. 12A and in its axially stretched configuration in FIG. 12B.
Figure 12B:
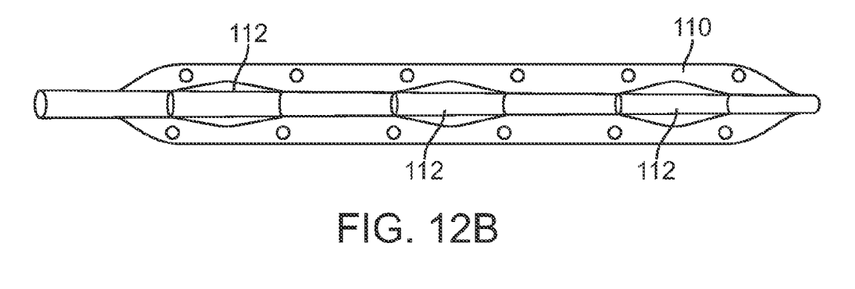

As shown in FIGS. 12A and 12B, a film 110 may include a plurality of lateral slits 112, were the lateral slits 112 allow the film 110 to stretch greater in the axial direction, as shown in FIG. 12B, than would have been possible in the absence of the slits. In this way, the film can be caused to neckdown to a reduced profile relative to the non-slitted film.

Figure 13:
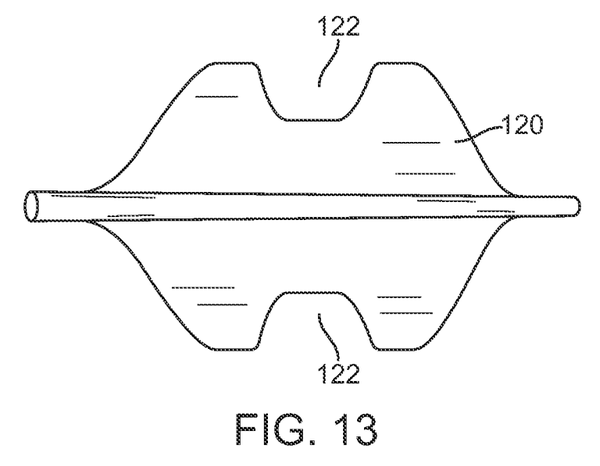
FIGS. 13-18 illustrate additional flat films geometric, suitable for use in the luminal occlusion devices of the present invention.
Figure 14:
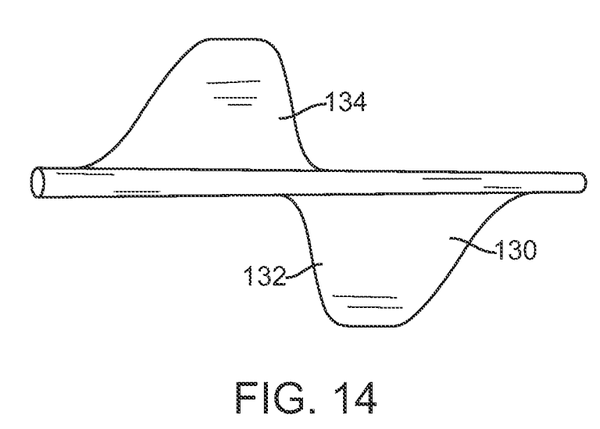
Figure 15:
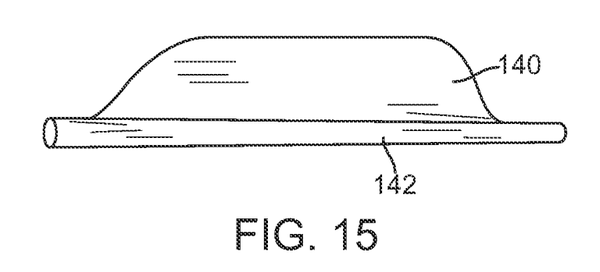
Figure 16:
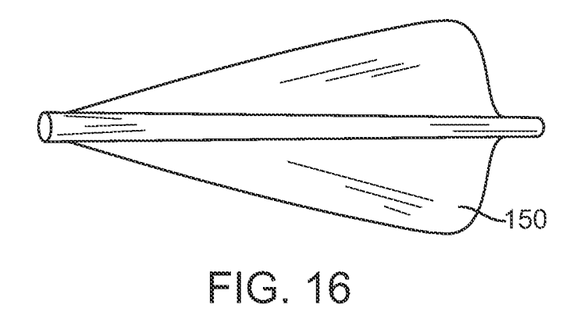
Figure 17:
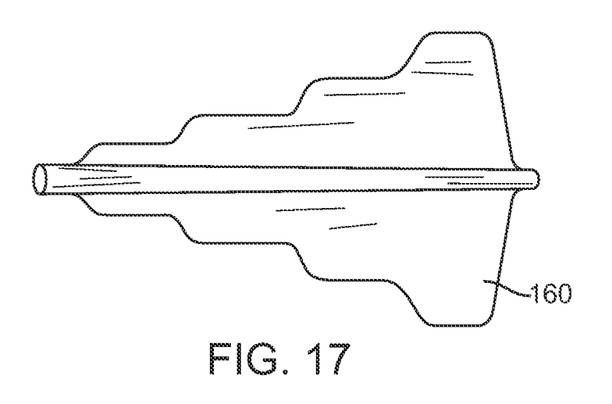
Figure 18:
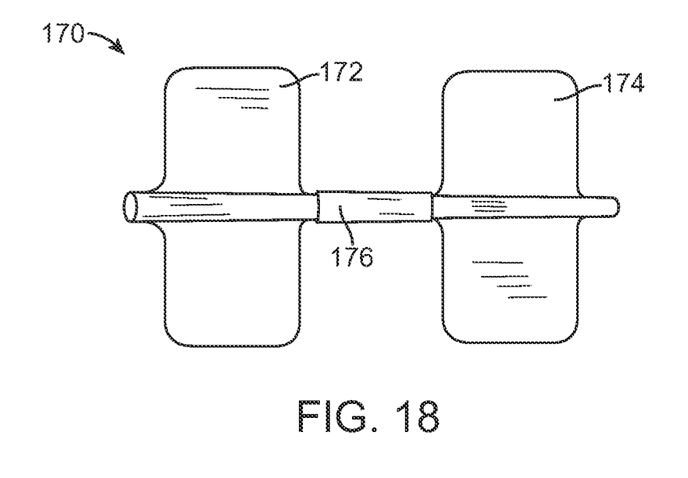

As shown in FIGS. 13-18, the films of the present invention may have a variety of peripheral shapes. As shown in FIG. 13, a film 120 has a symmetric profile with a gap 122 along each edge. As shown in FIG. 14, a film 130 comprises a pair of axially staggered wings 132 and 134 so that the film has an asymmetric profile. As shown in FIG. 15, a film 140 consists of a single wing on one side of the axial receptacle 142. As shown in FIGS. 16 and 17, films may have tapered profiles. In FIG. 16, film 150 has smoothly tapered edges. As shown in FIG. 17, film 160 has stepped, tapered edges. As shown in FIG. 18, a film 170 may comprise two or more axially separated segments 172 and 174. The films 172 and 174 are separated by a non-collapsible spacer 176 so that after compaction, each of the segments 172 and 174 will form a separate occlusion component with a fixed space therebetween.

Figure 19:
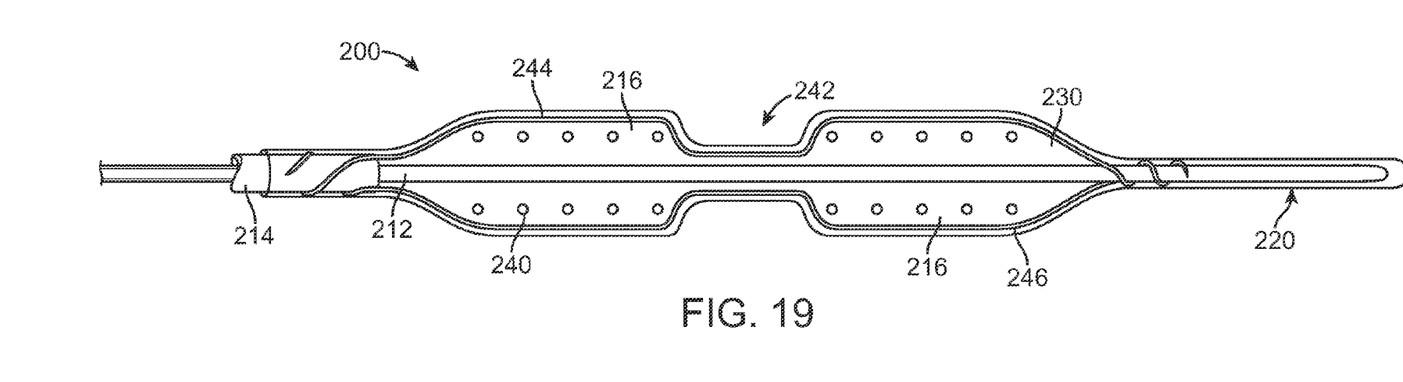
FIGS. 19 and 20 illustrate a specific embodiment of a luminal occlusion device constructed in accordance with the principles of the present invention and having two axially spaced-apart winged regions (FIG. 19) which may be axially collapsed into two axially spaced-apart compacted structures (FIG. 20).
Figure 20:
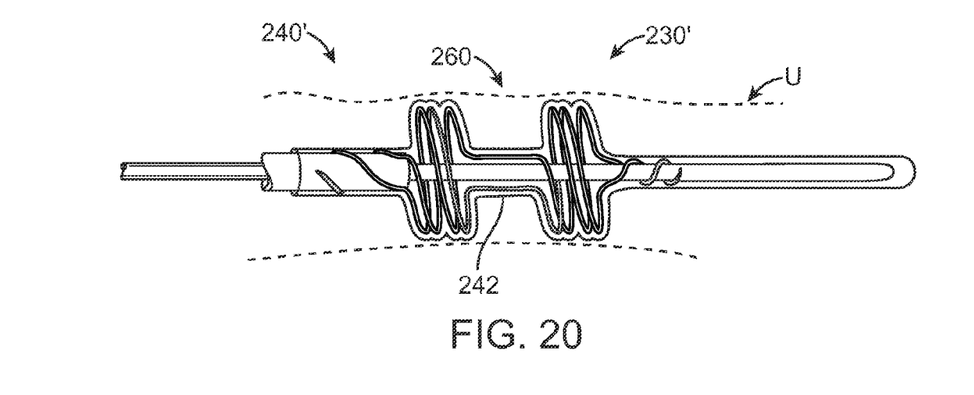

Referring now to FIGS. 19 and 20, a further exemplary luminal occlusion device 200 comprises a tension member 212, and elongate shaft 214, a flat film 216, a handle (not shown), and a distal tip 220. While the structure of the luminal occlusion device is generally the same as for the luminal occlusion device 10 illustrated in FIGS. 1, 2, and 3A-3D, except that the flat film 216 includes a first or distal wing portion 230 and a second or proximal wing portion 240. The wing portions 230 and 240 are separated by a narrowed or waist region 242 therebetween. Elastic wires 244 and 246 are disposed along the outer edges of both the wing portions 230 and 240 as well as the narrowed region 242. The wires will be configured to maintain the flat film 216 in its pre-deployment or flattened configuration as illustrated in FIG. 19. They will further be configured to cause the wing portions 230 and 240 to collapse into compacted regions 230' and 240', as illustrated in FIG. 20 as the tension member is proximally retracted relative to the elongate shaft 214. Preferably, the narrowed region 242 will be reinforced or otherwise prevented from collapsing so that the length of the narrowed region remains more or less constant so that the compacted regions 230' and 240' are maintained in their axially spaced-apart configuration, as shown in FIG. 20. The narrowed region thus provides a space or volume 260 when the occlusion device is deployed in a ureter U or other body lumen, also as shown in FIG. 20. The space or volume can isolate urinary calculi or stones or serve other purposes in performing intraluminal medical procedures.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A luminal occlusion device comprising:
   a tension member having a proximal end and a distal end;
   an elongate shaft having a guide structure along at least a distal portion thereof for receiving the tension member and permitting the tension member to shift between a distally extended position and a proximally retracted position relative to the shaft; and
   a flat film having an axial receptacle for receiving a distal portion of the tension member, a first wing on one side of the receptacle, and a second wing on the other side of the receptacle, wherein a distal end of the film is attached to a distal location on the tension member and a proximal end of the film is attached to a distal end of the elongate shaft,
   a first elastic wire extending along an outer peripheral edge of the first wing and a second elastic wire extending along an outer peripheral edge of the second wing, each wire movably coupled at a distal end to the tension member and at a proximal end to the elongate shaft,
   wherein proximally translating the tension member relative to the shaft axially compacts the wires to compact the flat film and distally translating the tension member relative to the shaft straightens the wires to stretch the film.

2. A device as in claim 1, wherein the peripheral edges are parallel and spaced apart by a distance in the range from 2 mm to 15 mm.

3. A device as in claim 2, wherein the flat film has a length in the axial direction in the range from 10 mm to 100 mm when the tension member is neither proximally nor distally translated.

4. A device as in claim 3, wherein prior to compacting, the flat film comprises a polymeric sheet structure having a total thickness in the range from 0.1 mm to 0.5 mm.

5. A device as in claim 1, wherein the flat film comprises at least one radioopaque marker formed on a surface thereof 6. A device as in claim 5, wherein the flat film comprises at least two radioopaque markers, with one disposed on each side of the axial receptacle.

7. A device as in claim 5, wherein the flat film comprises a plurality of individual radiopaque markers arranged in a line parallel to the outer peripheral edge of each wing.

8. A device as in claim 7, wherein the radioopaque markers comprise gold foil strips.

9. A device as in claim 1, wherein the elastic wires are composed of a highly elastic alloy.

10. A device as in claim 1, wherein the first and second elastic wires are radioopaque.

11. A device as in claim 1, wherein the first and second elastic wires bias the flat film radially outward from the axial receptacle.

12. A device as in claim 1, wherein the first and second elastic wires assume a helical configuration as the tension member is proximally translated.

13. A device as in claim 1, wherein the flat film includes a third wing portion aligned with but spaced proximally apart from the first wing portion and a fourth wing portion aligned with but spaced proximally of the second wing portion.

14. A device as in claim 13, wherein the first elastic wire is disposed continuously along the outer edges of the first and third wing portions and the second elastic wire is disposed continuously along the outer edges of the second and fourth wing portions.

15. A device as in claim 14, wherein the first and second elastic wires assume two axially spaced-apart helical configurations as the tension member is proximally translated.

16. A device as in claim 1, further comprising a distal tip extending distally from the distal end of the tension member.

17. A device as in claim 16, wherein the distal tip comprises a polymeric tube which tapers down in the distal direction.

18. A device as in claim 17, wherein the polymeric tube comprises polyurethane having a durometer in the range from 25 D to 55 D.

19. A device as in claim 1, wherein the tension member comprises a solid core wire.

20. A device as in claim 19, wherein the solid core wire comprises stainless steel with a width in the range from 0.2 mm to 0.6 mm.

21. A device as in claim 1, wherein the elongate shaft comprises a polymeric tube having an outside width in the range from 0.5 mm to 1.5 mm and a length in the range from 50 cm to 250 cm.

22. A device as in claim 21, wherein the polymeric tube comprises polyether block amide having a durometer in the range from 50 D to 80 D.

23. A device as in claim 22, wherein at least a portion of the polymeric tube is reinforced.

24. A device as in claim 23, wherein the entire length of the polymeric tube is reinforced with a steel braid.

25. A device as in claim 1, further comprising a handle assembly at the proximal end of the elongate shaft.

26. A device as in claim 25, further comprising a grip at the proximal end of the tension member.

27. A device as in claim 26, wherein the handle is removably attached to the proximal end of the shaft and the grip can be covered by the handle when the tension member is positioned fully distally relative to the shaft.

28. A device as in claim 1, further comprising a detent near the proximal end of the tension member, wherein the detent expands when the tension member is proximally retracted to deploy the film and wherein the expanded detent inhibits inadvertent distal movement of the tension member after deployment.

29. A device as in claim 28, wherein the detent comprises one or more bends in the tension member.

30. A device as in claim 1, wherein the flat film has one or more slits.

31. A device as in claim 30, wherein the slits are oriented axially to facilitate radial expansion when the film is compacted.

32. A device as in claim 30, wherein the slits are oriented laterally to facilitate stretching as the tension member is distally translated.

33. A device as in claim 1, wherein the flat film is arranged symmetrically on either side of the axial receptacle.

34. A device as in claim 1, wherein the flat film is arranged asymmetrically on either side of the axial receptacle.

35. A device as in claim 1, wherein at least a distal edge of each wing of the flat film has a tapered profile.

* * * * *